United States Patent [19]

Simonov et al.

[11] 4,189,575

[45] Feb. 19, 1980

[54] HALOGENATED SPIRO COMPOUNDS

[76] Inventors: Valery V. Simonov, ulitsa Bljukhera, 14, kv. 20; Anatoly F. Anischenko, ulitsa Bljukhera, 18, kv. 48; Emilia N. Popova, ulitsa Bljukhera, 14, kv. 13; Tamara P. Dunaeva, ulitsa Bljukhera, 14, kv. 63; Raif T. Gazizov, ulitsa Mira, 23, kv. 36; Vadim D. Simonov, ulitsa Bljukhera, 18, kv. 38, all of Ufa, U.S.S.R.

[21] Appl. No.: 871,454

[22] Filed: Jan. 23, 1978

[30] Foreign Application Priority Data

Feb. 1, 1977 [SU] U.S.S.R. .............................. 2449178

[51] Int. Cl.² .................... C07C 265/38; C07C 49/54; C07C 49/80; C07C 87/45
[52] U.S. Cl. ......................................... 544/70; 71/88; 71/21; 71/123; 260/563 P; 260/576; 260/586 G; 260/590 B; 424/248; 424/57; 424/325; 424/331
[58] Field of Search ........... 260/586 G, 590 B, 563 P, 260/576; 544/70

[56] References Cited

U.S. PATENT DOCUMENTS

| | | | |
|---|---|---|---|
| 2,584,139 | 2/1952 | Lidov et al. ..................... | 260/596 G |
| 3,875,236 | 4/1975 | Little et al. ..................... | 260/586 G |

FOREIGN PATENT DOCUMENTS 1022865  3/1966  United Kingdom ................ 260/586 G

OTHER PUBLICATIONS

Roedig, "Ann", 1950, vol. 569, No. 3, p. 161.
McBee et al., "JACS", vol. 77, No. 16, p. 4379 (1955).

*Primary Examiner*—Norman Morgenstern
*Attorney, Agent, or Firm*—Steinberg & Blake

[57] ABSTRACT

Halogenated spiro compounds of the formula:

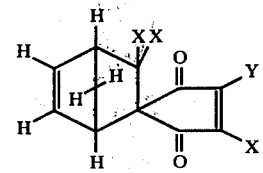

wherein X is Cl, Y is Cl, p-chlorophenoxy,

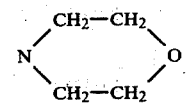

or

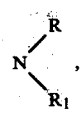

wherein R is H, $R_1$ is H, alkyl, alkenyl, cycloalkyl, aralkyl, aryl, or m-bromophenyl. The compounds according to the present invention exhibit fungicidal and bactericidal activity and can be used against various plant diseases as well as molding of non-metallic materials.

9 Claims, No Drawings

HALOGENATED SPIRO COMPOUNDS

FIELD OF THE INVENTION

The present invention relates to novel compounds, viz. halogenated spiro compounds.

SUMMARY OF THE INVENTION

The compounds according to the present invention have the following formula:

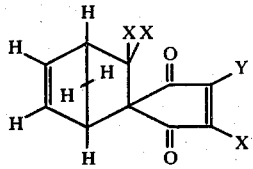

wherein X is chlorine, y is chlorine, p-chlorophenoxy

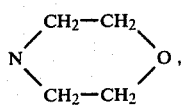

or

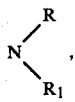

wherein R is H, $R_1$ is hydrogen, alkyl, aleknyl, cycloalkyl, aralkyl, aryl, m-bromophenyl.

Halogenated spiro compounds of the above-given formula exhibit fungicidal and bactericidal activity and may be used for treating various plant diseases as well as molding of non-metallic materials.

The most active, among these compounds, is 3,3-dichloro-5-norbornene-2-spiro-[2'-(4',5'-dichloro-4'-cyclopentene-1'-3'-dione] hereinafter referred to as compound A.

This compound is especially efficient as a fumigation agent for the treatment of grains of crops for smut control; it is also a good disinfecting agent against grain molding; it also hinders the development of root rots.

Detailed Description of the Invention

This compound is prepared by reacting cyclopentadiene with perchloro-2-methylene-4-cyclopentene-1,3-dione in a medium of an organic solvent at a temperature within the range of from 30° to 60° C. in the presence of a polymerization inhibitor according to the following scheme:

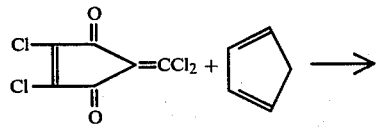

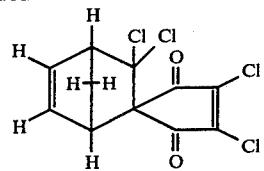

As organic solvents use can be made of non-polar and polar organic solvents such as benzene, acetone, ethylacetate, carbon tetrachloride, toluene, dioxane.

To increase the product yield and improve its quality, it is advisable to carry out the reaction in an excess of cyclopentadiene.

Increasing temperature above 60° C. results in an accelerated reaction of dimerization of cyclopentadiene, whereby the yield of the desired product is reduced.

Reducing temperature below 30° C. substantially lowers the reaction rate.

As polymerization inhibitors use can be made of, for example, hydroquinone, pyrocatechol, pyrogallol.

The remaining compounds corresponding to the above-given general formula, except compound A, are prepared by treating compound A, i.e. 3,3-dichloro-5-norbornene-2-spiro-[2'-(4',5'-dichloro-4'-cyclopentene-1',3'-dione)] with morpholine, p-chlorophenol or amines of the formula

wherein R is hydrogen, $R_3$ is hydrogen, alkyl, alkenyl cycloalkyl, aralkyl, aryl, or m-bromophenyl which enables substitution of one atom of chlorine in the cyclopentene ring with said radicals. The treatment is conducted at a temperature within the range of from 20° to 30° C. in a medium of an organic solvent.

Amines of the general formula

may be exemplified by ammonia, alkylamines containing 1 to 4 carbon atoms alkenylamines containing 3 to 5 carbon atoms, cycloalkylamines containing 5 to 6 carbon atoms, benzylamine, phenylamine or halogenated phenylamine.

The thus-produced compounds comprise solid crystalline products which are colourless or slightly yellow-coloured and have a melting point within the range of from 120° to 210° C., and are soluble in organic solvents and insoluble in water.

The structure of the thus-produced compounds corresponding to the above-given general formula is proven by elemental analysis as well as by data of mass-spectrometry, UV and IR spectra.

The compounds according to the present invention may be used both individually and in the form of compositions incorporating these compounds along with corresponding carries, surfactants and other ingredients.

The carriers may be of inorganic, organic, synthetic or natural origin.

The carriers may be either solid (china clay, chalk, limestone, talc, bentonite, solid fertilizers such as ureas, microelements and the like) or liquid (water, cyclohexanone, solvent and the like). As a surfactant use can be made of a wetting agent, an emulsifying agent or a dispersing agent.

Use can be made of various surfactants such as products of condensation of alkylphenols with ethylene oxide or propylene oxide or both, sulphates or sulphonates of said condensation products, lignosulphates of sodium or calcium.

As other ingredients use can be made, for example, of protective colloids, stabilizing agents, binders, fertilizers other fungicides or pesticides and the like.

Preparative forms of the compounds according to the sent invention may involve powders, granules, pellets.

Powders are prepared by intermixing and grinding of the compounds according to the present invention, a solid carrier, surfactants and other ingredients.

Granules are prepared by agglomeration or impregnation so that they have a diameter of from 2.8 to 3.0 mm and a length of 3 to 5 mm. In the preparation of pellets the compounds according to the present invention, a filler and other ingredients are intermixed, wetted, applied onto the treated article and dried.

Fungicidal and bactericidal effect of the compositions may be enlarged by the addition of the following compounds: hexachlorobenzene, tetramethylthiuramdisulphide, 6-methyl-2,3-dihydro-1,4-oxathiine-5-carbanilide; N-trichloromethylmercapto-1,2,3,6-tetrahydrophthalimide; 2,4,5-trichlorophenol 2,4-dinitrophenol; N,N'-ethylene-bis zinc dithiocarbamate; double salt of N,N'-ethylene-bis-dithiocarbamoyldisulphide; 2,3-dichloronaphtoquinone-1,4, copper oxychloride and the like.

The compounds according to the present invention have been tested for biological activity on cultures of phytopathogenic fungi and bacteriae on seeds of wheat, oats, proso, corn, and peas against infectants causing molding of said plants, root rots as well as in the treatment of smut diseases and against fungi deteriorating non-metallic materials.

Spores of fungi *Fusarium solani, Helminthosporium sativum, Alternaria tenuis, Botrytis cinerea* and bacteriae *Xanthomonas malvacearum* are grown in an aqueous suspension of the compounds according to the present invention (at the temperature of 24° C. for the period of 20 hours) containing 0.005% by weight of the compound or inoculated onto a nutritive medium containing 0.003% by weight of the compound and maintained at the temperature of 24° C. for 72 hours. The effect of the compounds on sprouting of spores and growth of colonies of fungi or bacteria is then evaluated.

The test results shown in Table 1 show toxicity of the compounds according to the present invention with respect to the above-listed fungi and bacteria.

The most toxic with respect to fungi is 3,3-dichloro-5-norbornene-2-spiro-[2'-(4',5'-dichloro-4'-cyclopentene-1',3'-dione)] referred to as compound A.

Fungitoxic properties of compound A on various cultures are shown hereinbelow.

Effect of compound A on fungi causing diseases of seeds of crops

Seeds of wheat naturally infected with fungi causing black germ and molding (*Helminthosporium sativum, Alternaria tenuis, Fusarium culmorum, Penicillium sp., Cladosporium sp., Mucor sp.*) are treated with compound A at a rate of 1-1.5 g of compound A per 1 kg of seeds while wetting with water (10 ml/kg) or pelletized and 2-3 days after are placed for sprouting into a humid chamber (Petri dishes lined with filtering paper) at the temperature of 25° C. 7 days after the degree of infection of the seeds with fungi is determined.

The test results obtained in this experiment are shown in Table 2 hereinbelow.

Effect of compound A on fungi causing diseases of seeds of corn and pea

Corn seeds infected with *Aspergillus flavus* and seeds of pea infected with *Fusarium avenaceum* are treated with compound A (2 g of the compound per kg of the seeds) and sprouted at the temperature of 25° C. for the period of 7 days.

The test results are shown in Table 3 hereinbelow.

Effect of compound A on conidia *Venturia* inaequalis

Apple leaves infected with scab are treated with a 0.1% suspension of compound A. After 2-5 days there are isolated conidia of the infectant of the disease and grown in water at the temperature of 24° C. for the period of 48 hours. Compound A completely kills conidia *Venturia* inaequalis.

The test results are shown in Table 4 hereinbelow.

Effect of compound A on molds

The test is performed following three procedures referred hereinafter as procedures A, B, and C.

Method A: The Chapek nutritive medium is inoculated with a mixture of fungi *Aspergillus niger, Chaetomium globosum, Penicillium funiculosum, Penicillium cyclopium, Paecilomyces varioti.*

Onto the lawn-type inoculate of fungi there is applied, in three spots, compound A in the amount of 15 mg (diameter 10 mm), incubated at the temperature of 28° C. and after 7-14 days the zone of fungi growth inhibition around the compound is evaluated on a point scale.

Method B: The test is conducted in a manner similar to that of Method A, except that saccharose is added into the Chapek nutritive medium.

Method C: Into the Chapek nutritive medium on agar (2% by weight) there is added 0.1% by weight of compound A, the mixture is stirred and poured into Petri dishes, 25 ml in each. Onto the congelated medium there is inoculated, in several spots (3-4 spots), the mixture of the above-mentioned fungi. The degree of fungi growth inhibition is evaluated to determine the effect of the compound according to the present invention. The test results are shown in Table 5 hereinbelow.

Effect of compound A on *Ustilago avenae, Ustilago levis Sphacelotheca panici-miliacei* and *Fusarium oxysporum*

Seeds of oats and proso are artifically infected with chlamydospores of *Ustilago levis, Ustilago avenae,* and *Sphacelotheca panici-miliacei,* at the rate of 2 g per 1 kg of the seeds and treated with the compound of the present invention at the rate of 1-1.5 kg per 1 ton prior to sowing or 3-4 months prior to sowing. Infection with *Fusarium oxysporum is natural. The wet treatment of the seeds is effected with water* (10 l/ton). The test results are shown in Tables 6 and 7 hereinbelow.

As follows from Tables 1 to 7, the compounds according to the present invention display fungicidal and bactericidal activity. An especially wide range of activity is characteristic of compound A, wherein X and Y are each chlorine. It is highly toxic for fungi pertaining to the class of *ascomycetes, basidiomycetes, deuteromy-*

*cetes, phycomycetes* causing plant diseases and molding of non-metallic materials and, more specifically, *Venturia inaequalis, Tilletia caries, Ustilago avenae, Ustilago levis, Ustilago hordei, Sphacelotheca panici-miliacei, Fusarium solani, Fusarium oxysporum, Fusarium culmorum, Fusarium avenaceum, Helminthosporium sativum, Alternaria tenuis, Botrytis cinerea, Trichothecium roseum, Cladosporium herbarum, Aspergillus niger, Aspergillus flavus, Chaetomium globosum, Penicillium funiculosum, Penicillium cyclopium, Paecylomices varioti, Mucor sp.,* and inhibits the growth of bacteria *Xanthomonas malvacearum.*

For a better understanding of the present invention some specific Examples illustrating the method of preparing compounds according to the present invention are given hereinbelow.

EXAMPLE 1

Preparation of 3,3-dichloro-5-norbornene-2-spiro-[2'(4',5'-dichloro-4'-cyclopentene-1',3'-dione)].

Into a three-neck flask provided with a stirrer, thermometer, and a reflux condenser there are charged 12.3 g (0.05 mole) of perchloro-2-methylene-4-cyclopentene-1,3-dione, 19.8 g (0.3 mole) of cyclopentadiene and 0.1 g of hydroquinone. This suspension is heated to a temperature of from 35° to 40° C. under stirring for 3 hours. Then the solid particles are filtered-off, washed with n-heptane or gasoline and dried. In this manner there are obtained 14 g (90%) of pure crystals of Compound A (X=Y=Cl with the melting point 129°–130° C.

IR-spectrum, cm$^{-1}$: 1,598; 1,730.
Mass-spectrum, m/e: 310 (M+).

EXAMPLE 2

Preparation of 3,3-dichloro-5-norbornene-2-spiro-[2'-(4'-allylamino-5'-chloro-4'-cyclopentene-1',3'-dione)].

Into a four-neck flask provided with a stirrer, thermometer, reflux condenser and a dropping funnel there are charged 15.6 g (0.05 mole) of compound A (X=Y=Cl) prepared in the foregoing Example 1 and 80 ml of benzene. This mixture is dropwise added, over 0.5 hour, with a solution of 5.7 g (0.1 mole) of allylamine in 20 ml of benzene under stirring at room temperature; the stirring is then continued for additional hour. Thereafter, the reaction mass is twice extracted with 100 ml of water, benzene is distilled-off from the organic layer, the residue is washed with acidified water, then with water and dried. There are obtained 15.8 g (95%) of a crude product. After double recrystallization from heptane there are obtained yellow crystals of said compound (X=Cl, Y=NH—CH$_2$—CH=CH$_2$) with the melting point of 116°–117° C.

IR-spectrum, cm$^{-1}$: 1,590; 1,640; 1,725; 3,350.
Mass-spectrum, m/e: 331 (M+).

EXAMPLE 3

Preparation of 3,3-dichloro-5-norbornene-2-spiro-[2'-(4'-amino-5'-chloro-4'-cyclopentene-1,3-dione)].

The product prepared in Example 1 hereinbefore is charged into a flask and added with benzene as in the foregoing Example 2. Then, gaseous ammonia is passed over 4 hours into the benzenic solution and the further treatment is conducted as in Example 2. There are obtained 90% of the final product (X=Cl, Y=NH$_2$) with the melting point of 165°–167° C.

IR-spectrum, cm$^{-1}$: 1,595; 1,728; 3,405.
Mass-spectrum, m/e: 291 (M+).

EXAMPLE 4

Preparation of 3,3-dichloro-5-norbornene-2-spiro-[2'-(4'-cyclohexylamino-5'-chloro-4'-cyclopentene-1'-3'-dione)].

The experiment is conducted following the procedure described in the foregoing Example 2. From 15.6 g (0.05 mole) of compound A (X=Y=Cl) and 9.9 g (0.1 mole) of cyclohexylamine there are produced 17.7 g (95%) of a crude product. After recrystallization from benzene there are obtained yellow crystals of the above-mentioned compound (X=Cl,

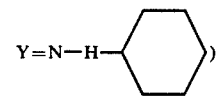

with the melting point of 206°–207° C.
IR-spectrum, cm$^{-1}$: 1,596; 1,735; 3,328.
Mass-spectrum, m/e: 373 (M+).

EXAMPLE 5

Preparation of 3,3-dichloro-5-norbornene-2-spiro-[2'-(4'-morpholino-5'-chloro-4-cyclopentene-1',3'-dione)].

The experiment is carried out following the procedure described in the foregoing Example 2. From 15.6 g (0.05 mole) of compound A (X=Y=Cl) and 8.72 g (0.1 mole) of morpholine there are obtained 16.4 g (91%) of a crude product. After a double recrystallization from ethanol there are produced greenish crystals of the above-mentioned compound (X=Cl,

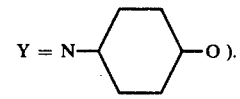

Melting point of the compound is 122°–124° C.
UV-spectrum, $\lambda_{max}$, nm: 258; 330.
Mass-spectrum, m/e: 378 (M+).

EXAMPLE 6

Preparation of 3,3-dichloro-5-norbornene-2-spiro-[2'-(4'-p-chlorophenoxy-5'-chloro-4'-cyclopentene-1',3'-dione)].

Into a flask provided with a stirrer, and a reflux condenser there are charged 15.6 g (0.05 mole) of compound A (X=Y=Cl), 6.4 g (0.05 mole) of p-chlorophenol, 5.1 g (0.05 mole) of triethylamine and 100 ml of benzene. After stirring for 2 hours the precipitated triethylamine hydrochloride is filtered-off and the benzenic filtrate is evaporated. After recrystallization of the compound from ethanol there are obtained 13 g (64.5%) of yellow crystals of the above-mentioned compound (X=Cl,

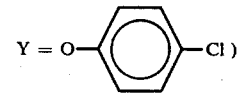

with the melting point of 152°–154° C. Repeated recrystallization from carbon tetrachloride gives melting point of 154°–155.5° C.
IR-spectrum, cm$^{-1}$: 1,628; 1,745; 3,327.

Mass-spectrum, m/e: 381 (M+).

EXAMPLE 7

Preparation of 3,3-dichloro-5-norbornene-2-spiro-[2'-(4'-n-butyl-amino-5'-chloro-4'-cyclopentene-1',3'-dione)].

Into a three-neck flask provided with a stirrer, thermometer and a reflux condenser there are charged 12.3 g (0.05 mole) of perchloro-2-methylene-4-cyclopentene-1,3-dione, 3.63 g (0.055 mole) of cyclopentadiene, 0.05 g of pyrocatechol and 50 ml of benzene. The reaction mixture is heated to the temperature of 50° C. under stirring for 2 hours. Then benzene is distilled-off as an azeotrope with water; the precipitate is filtered-off, washed and dried to give 11.35 g (73%) of yellow crystals of compound A (X=Y=Cl) with the melting point of 129°-130° C. Then there are taken 15.6 g of the resulting compound A (0.05 mole) (and 7.3 g (0.1 mole) of n-butylamine and the experiment is conducted as in Example 2 hereinbefore, to give 15.6 g (90%) of a crude product. After recrystallization from benzene there are obtained yellow crystals of said compound with the melting point of 150°-151° C. (X=Cl, Y=NH—nC$_4$H$_9$).

EXAMPLE 8

Preparation of 3,3-dichloro-5-norbornene-2-spiro-[2'-(4'-benzylamino-5'-chloro-4'-cyclopentene-1',3'-dione)].

Compound A is prepared as in Example 7, except that acetone is used as a solvent. There are employed 15.6 g (0.05 mole) of compound A, 11.3 g (0.1 mole) of benzylamine and the experiment is conducted as in Example 2 to give 12.6 g (65%) of a crude product. After recrystallization said compound is obtained with the melting point of 135°-135.5° C. Characteristics of the resulting compounds are given in Table 8 hereinbelow.

Table 1

Fungicidal and bactericidal activity of compounds of the formula

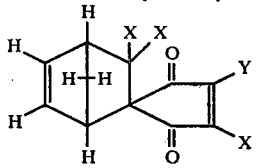

| No. | X | Y | Concentration of the biological-lz active compound | F. solani | H. sativum | A. tenuis | B. cinerea | Concent. of biol. active compound, % | F. solani | H. sativum | A. tenuis | B. cinerea | X. maliacear |
|---|---|---|---|---|---|---|---|---|---|---|---|---|---|
| | | | | Inhibition of growth of fungi spores,% | | | | | Inhibition of growth of colonies | | | | |
| 1. | Cl | Cl | 0.005 | 100.0 | 100.0 | 100.0 | — | 0.003 | 75.1 | 100.0 | 100.0 | — | 62.5 |
| 2 | Cl | NH$_2$ | " | 20.1 | 62.5 | 3.5 | — | " | 9.0 | 28.9 | 0.7 | — | 25.1 |
| 3. | Cl | NH—cyclohexyl | " | 3.5 | 80.0 | 3.5 | — | " | 3.0 | 23.8 | 3.6 | — | 42.0 |
| 4. | Cl | NH—phenyl | " | 16.1 | 40.0 | 0.0 | — | " | 7.0 | 30.8 | 14.4 | — | 28.5 |
| 5. | Cl | NH—CH$_2$—CH=CH$_2$ | " | 6.0 | 65.0 | 3.5 | — | " | 21.0 | 41.6 | 33.1 | — | 49.2 |
| 6. | Cl | NH—(4-Cl-phenyl) | " | 55.8 | — | — | 0 | " | 52.1 | — | — | 36.7 | — |
| 7. | 2,3-dichloronaphthoquinone (standard) | | " | 100.0 | 100.0 | 100.0 | — | " | 42.3 | 85.9 | 75.1 | — | 28.3 |

Sprouting of spores in the control, %
F. solani — 97.5-100
H. sativum — 85-95
A. tenuis — 87-94
B. cinerea — 98-99

Table 2

Toxicity of compound A for fungi affecting wheat seeds in comparison with ethylmercurychloride

| Fungicide | Rate of application of the biologically active compound, g/kg of seeds | Germination capacity of seeds, % | Affection of seeds with fungi, % | | | |
|---|---|---|---|---|---|---|
| | | | Total including | | | |
| | | | H. sativum | F. culmorum | A. tenuis | Penicillium Cladosporium |
| Compound A | 1.5 | 98.0 | 5.2 | 0.6 | 0.3 | 0.1 | 4.2 |
| Ethylmercurychloride (prior art fungicide, for comparison) | 2.0 (calculated for the preparation) | 88.0 | 8.3 | 1.1 | 0.0 | 0.7 | 6.5 |

Table 2-continued

Toxicity of compound A for fungi affecting wheat seeds in comparison with ethylmercurychloride

| Fungicide | Rate of application of the biologically active compound, g/kg of seeds | Germination capacity of seeds, % | Affection of seeds with fungi, % Total including | H. sativum | F. culmorum | A. tenuis | Penicillium Cladosporium |
|---|---|---|---|---|---|---|---|
| Control (without treatment) | — | 96.0 | 46.5 | 13.3 | 17.9 | 1.1 | 14.2 |

Table 3

Efficiency of compound A in desinfection of seeds of corn and pea against mold fungi

| Fungicide | Application rate of biologically active compound, g/kg of seeds | Affection of seeds of corn A. flavus, % | Affection of seeds of pea F. avenaceum, % |
|---|---|---|---|
| Compound A | 2.0 | 2.0 | 32.0 |
| Tetramethylthiuram-disulphide (prior art fungicide for comparisons) | 2.0 | 80.0 | 100.0 |
| Control (without treatment) | — | 99.0 | 100.0 |

Table 4

Toxic effect of compound A on conidia of fungi V. inaequalis

| Fungicide | Concentration of biologically active compound, % | Growth of conidia in water, % 2 days after treatment of trees | 5 days after treatment of trees |
|---|---|---|---|
| Compound A | 0.3 | 0 | 0 |
| N,N'-ethylene-bis-dithiobarbamate of zinc (prior art fungicide for comparison) | 0.5 | 15.2 | 17.0 |
| Control (without treatment) | — | 76.0 | 76.3 |

Table 5

Toxic effect of compound A on mold fungi affecting non-metallic materials

| No. | Fungicide | Dose of biologically active compound, mg | A Fungi growth, points | B Fungi growth, points | C Concentration of biologically active compound, % | Inhibition of growth of fungi mycellium, % |
|---|---|---|---|---|---|---|
| 1. | Compound A | 15.0 | 0 | 0 | 0.1 | 100.0 |
|  |  | — | — | — | 0.01 | 100.0 |
| 2. | N-trichloromethyl-mercapto-1,2,3,6-tetrahydrophthalimide (prior art fungicide for comparison) | — | 0 | 0 | 0.1 | 100.0 |
|  |  | 15.0 | — | — | 0.01 | 100.0 |
| 3. | Control (without antiseptic) | — | 3 | 3 | — | — |

0 - absence of growth
1 - weak growth observed in microscope
2 - moderate growth visually observed
3 - good growth

Table 6
Efficiency of compound A against smut and root rots of proso in comparison with ethylmercury chloride

| Fungicide | Application rate of the biologically active compound, kg/t of seeds | Field germination of seeds, % | Stand density, plants/m² | Affection with smut % | Affection with root rots, % | Yield pf crops, c/ha |
|---|---|---|---|---|---|---|
| Compound A | 1.5 | 85.1 | 359 | 0.5 | 0.6 | 42.3 |
| Ethylmercurychloride (prior art fungicide for comparison) | 2.0 (calculated for the composition) | 83.8 | 359 | 0.5 | 2.3 | 38.9 |
| Control (without treatment) | — | 81.0 | 342 | 31.4 | 4.6 | 35.4 |

Table 7
Efficiency of compound A against loose and covered smut of oats in comparison with ethylmercurychloride

| Fungicide | Application rate of the biologically active compound, kg/ton of seeds | Field germination of seeds, % | Stand density, plants/m² | Affection with smut, % | Yield of crops, c/ha |
|---|---|---|---|---|---|
| Compound A | 1.5 | 87.7 | 496 | 0.4 | 34.5 |
| Ethylmercurychloride (prior art fungicide for comparison) | 1.5 (calculated for the composition) | 93.4 | 530 | 0.4 | 33.3 |
| Control (without treatment) | — | 94.0 | 534 | 9.9 | 21.4 |

Table 8
Characteristics of compounds of the formula

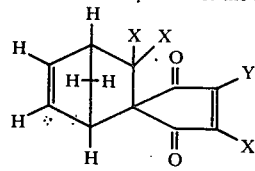

| No. | X | Y | °C. M.P. | Found, % by weight C | H | Cl | N | Calculated, % by weight C | H | Cl | N | Yield, % | Formula of the compound |
|---|---|---|---|---|---|---|---|---|---|---|---|---|---|
| 1. | Cl | —Cl | 130–131 | 41.9 | 2.30 | 45.9 | — | 42.4 | 1.90 | 45.6 | — | 90 | $C_{11}H_6O_2Cl_4$ |
| 2. | Cl | —NH₂ | 165–167 | 45.4 | 3.12 | 36.2 | 4.93 | 45.1 | 2.70 | 36.5 | 4.80 | 90 | $C_{11}H_8O_2NCl_3$ |
| 3. | Cl | —NH—CH₂—CH=CH₂ | 116–117 | 50.2 | 3.31 | 32.6 | 4.17 | 50.6 | 3.50 | 32.1 | 4.20 | 95 | $C_{14}H_{12}O_2NCl_3$ |
| 4. | Cl | —NH—(cyclohexyl) | 206–207 | 55.0 | 5.10 | 28.3 | 4.22 | 54.6 | 4.70 | 28.5 | 3.70 | 95 | $C_{17}H_{18}O_2NCl_3$ |
| 5. | Cl | —N(morpholino) | 122–124 | 49.3 | 4.29 | 28.9 | 3.50 | 49.8 | 3.90 | 29.3 | 3.90 | 91 | $C_{15}H_{14}O_3NCl_3$ |
| 6. | Cl | —O—C₆H₄—Cl | 154–155.5 | 50.0 | 2.68 | 35.1 | — | 50.4 | 2.58 | 35.5 | — | 64.5 | $C_{17}H_{10}O_3Cl_4$ |
| 7. | Cl | —NHC₄H₉-n | 150–151 | 51.2 | 4.01 | 29.93 | 4.10 | 51.65 | 4.59 | 30.56 | 4.02 | 90.0 | $C_{15}H_{16}O_2NCl_3$ |

Table 8-continued
Characteristics of compounds of the formula

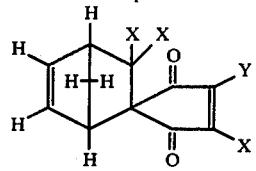

| No. | X | Y | °C. M.P. | Found, % by weight | | | | Calculated, % by weight | | | | Yield, % | Formula of the compound |
|---|---|---|---|---|---|---|---|---|---|---|---|---|---|
| | | | | C | H | Cl | N | C | H | Cl | N | | |
| 8. | Cl | —NH—CH₂—⬡ | 135–135.5 | 56.0 | 3.05 | 27.80 | 3.24 | 56.47 | 3.66 | 27.84 | 3.66 | 65.0 | $C_{18}H_{14}O_2NCl_3$ |
| 9. | Cl | —NH—⬡ | 170–172 | 55.4 | 3.78 | 28.5 | 3.95 | 55.3 | 3.30 | 28.9 | 3.80 | 87 | $C_{17}H_{12}O_2NCl_3$ |
| 10. | Cl | —NH—⬡—Br | 166–168 | 45.2 | 2.68 | 23.5 | 2.74 | 45.7 | 2.46 | 23.7 | 3.13 | 82 | $C_{17}H_{11}O_2NCl_3Br$ |

What is claimed is:

1. Halogenated spiro compounds of the formula:

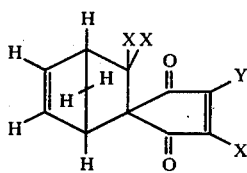

wherein X is Cl, Y is selected from the group consisting of Cl, p-chlorophenoxy,

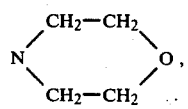

and

wherein R is H, and
$R_1$ is selected from the group consisting of H, alkyl, alkenyl, cycloalkyl, aralkyl, aryl and m-bromophenyl.

2. 3,3-dichloro-5-norbornene-2-spiro-[2'-(4',5'-dichloro-4'-cyclopentene-1',3'-dione)].

3. The compound of claim 1 wherein said compound is 3,3-dicholoro-5-norbornene-2-spiro-[2'-(4'-allylamino-5'-chloro-4'-cyclopentene-1',3'-dione)].

4. The compound of claim 1 wherein said compound is 3,3-dichloro-5-norbornene-2-spiro[2'-(4'-amino-5'-chloro-4'-cyclopentene-1',3'-dione)].

5. The compound of claim 1 wherein said compound is 3,3-dicholoro-5-norbornene-2-spiro-[2'-(4'-cyclohexylamino-5'-chloro-4'-cyclopentene-1'-3'-dione)].

6. The compound of claim 1 wherein said compound is 3,3-dichloro-5-norbornene-2-spiro-[2'-(4'-morpholino-5'-chloro-4-cyclopentene-1',3'-dione)].

7. The compound of claim 1 wherein said compound is 3,3-dichloro-5-norbornene-2-spiro-[2'-(4'-p-chlorophenoxy-5'-chloro-4'-cyclopentene-1',3'-dione)].

8. The compound of claim 1 wherein said compound is 3,3-dichloro-5-norbornene-2-spiro-[2'-(4'-n-butylamino-5'-chloro-4'-cyclopentene-1',3'-dione)].

9. The compound of claim 1 wherein said compound is 3,3-dichloro-5-norbornene-2-spiro-[2'-(4'-benzylamino-5'-chloro-4'-cyclopentene-1',3'-dione)].

* * * * *